(12) United States Patent
Güneysel

(10) Patent No.: US 8,283,645 B2
(45) Date of Patent: Oct. 9, 2012

(54) PARTICLE THERAPY INSTALLATION

(75) Inventor: Murat Güneysel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 163 days.

(21) Appl. No.: 12/676,317

(22) PCT Filed: Aug. 7, 2008

(86) PCT No.: PCT/EP2008/060369
§ 371 (c)(1),
(2), (4) Date: Mar. 3, 2010

(87) PCT Pub. No.: WO2009/033897
PCT Pub. Date: Mar. 19, 2009

(65) Prior Publication Data
US 2010/0171045 A1  Jul. 8, 2010

(30) Foreign Application Priority Data
Sep. 6, 2007  (DE) .......................... 10 2007 042 336

(51) Int. Cl.
G21F 7/005 (2006.01)
A61N 5/10 (2006.01)

(52) U.S. Cl. .................. 250/517.1; 250/505.1

(58) Field of Classification Search ............... 250/517.1, 250/505.1
See application file for complete search history.

(56) References Cited

U.S. PATENT DOCUMENTS

| | | | | |
|---|---|---|---|---|
| 4,833,335 A * | 5/1989 | McGinley et al. | ......... | 250/518.1 |
| 4,870,287 A * | 9/1989 | Cole et al. | ................... | 250/492.3 |
| 5,416,334 A * | 5/1995 | Knapp et al. | ................ | 250/515.1 |
| 5,851,182 A * | 12/1998 | Sahadevan | ................... | 600/407 |
| 6,529,577 B1 * | 3/2003 | Allen et al. | ...................... | 378/69 |
| 6,894,300 B2 * | 5/2005 | Reimoser et al. | .......... | 250/505.1 |
| 8,101,932 B2 * | 1/2012 | Bichay | ....................... | 250/517.1 |
| 8,139,705 B2 * | 3/2012 | Fehrenbacher et al. | ...... | 376/192 |
| 2002/0150214 A1 * | 10/2002 | Spahn | ........................... | 378/189 |
| 2005/0029472 A1 | 2/2005 | Ueno et al. | | |

(Continued)

FOREIGN PATENT DOCUMENTS

DE  10 2004 029 026 A1  12/2005

(Continued)

OTHER PUBLICATIONS

German Office Action for corresponding German Patent Application No. DE 10 2007 042 336.7-54 dated May 30, 2008 with English translation.
International Search Report for PCT/EP2008/060369 dated Dec. 5, 2008.
Written Opinion of the International Searching Authority (with Supplementary Sheet in English) for PCT/EP2008/060369 dated Dec. 2008.

(Continued)

Primary Examiner — David A Vanore
Assistant Examiner — Wyatt Stoffa
(74) Attorney, Agent, or Firm — Lempia Summerfield Katz LLC

(57) ABSTRACT

A particle therapy system that includes at least one irradiation chamber, in which an object is irradiated with a treatment beam, an antechamber, which is screened off from radiation occurring in the irradiation chamber and from which access is made to the irradiation chamber, and an access area, which leads to the irradiation chamber and connects the irradiation chamber to the antechamber, is provided. A support for a patient moves along a path of travel from the antechamber, through the access area, to the irradiation chamber. A radiation protection door is arranged in the access area, and the access area is configured geometrically in such a way that the path of travel in the access area is substantially rectilinear.

18 Claims, 2 Drawing Sheets

U.S. PATENT DOCUMENTS

| | | | |
|---|---|---|---|
| 2005/0166473 A1* | 8/2005 | Jorg | 52/67 |
| 2005/0218348 A1* | 10/2005 | Fehrenbacher et al. | 250/517.1 |
| 2007/0012888 A1 | 1/2007 | Bichay | |
| 2008/0023658 A1* | 1/2008 | Bichay | 250/517.1 |
| 2010/0193713 A1* | 8/2010 | Bichay | 250/517.1 |

FOREIGN PATENT DOCUMENTS

| | | |
|---|---|---|
| JP | 5-223987 | 9/1993 |
| JP | 2007-85875 A | 4/2007 |
| WO | WO 2004/013865 A1 | 2/2004 |
| WO | WO 2005/120640 A1 | 12/2005 |
| WO | WO 2007/009786 A1 | 1/2007 |

OTHER PUBLICATIONS

Su, Y. W. et al., "Radiation Protection of CSR," Proceedings of the Second Asian Particle Accelerator Conference, Beijing, China, 2001, 3 pages.

Agosteo, S. et al., "Shielding calculations for a 250 MeV hospital-based proton accelerator," Nuclear Instruments and Methods in Physics Research, A 374, 1996, pp. 254-268.

Agosteo, S., "Radiation Protection at Medical Accelerators," Radiation Protection Dosimetry, vol. 96, No. 4, Milano, Italy, 2001, pp. 393-406.

* cited by examiner

PARTICLE THERAPY INSTALLATION

The present patent document is a §371 nationalization of PCT Application Serial Number PCT/EP2008/060369, filed on Aug. 7, 2008, designating the United States, which is hereby incorporated by reference. This patent document also claims the benefit of DE 10 2007 042 336.7, filed Sep. 6, 2007, which is also hereby incorporated by reference.

BACKGROUND

The present embodiments relate to a particle therapy system.

In particle therapy, a particle beam including protons or heavy ions (e.g., carbon ions) is created with a suitable accelerator. The particle beam is guided in a radiation channel and exits via an exit window of the radiation channel into an irradiation chamber where the irradiation of a patient is undertaken. Depending on the design of the irradiation chamber, this can be done via a fixed beam exit window (e.g., fixed beam irradiation chambers) but also via a rotatable gantry to allow radiation from a number of angles.

The costs involved in generating and steering a particle beam are greater by comparison with conventional radiation methods such as, for example, with high-energy x-ray beams. In order to still be able to work efficiently, a particle therapy system usually includes a number of treatment chambers arranged in the vicinity of one another, in each of which patients can be irradiated. While an irradiation process is being carried out in one of the treatment chambers, patients can be prepared in the other treatment chambers for a subsequent irradiation session or can be removed after a completed irradiation. This enables sensible use to be made of times at which no irradiation is being carried out in an irradiation chamber.

The treatment chambers are usually arranged in a particle therapy system such that access to the treatment chambers is possible from a shared corridor and/or antechamber. Usually further chambers (e.g., therapy planning rooms, lounges for patients or doctors, preparation chambers and/or examination chambers of patients and similar chambers), which are used in the particle therapy system, can be entered from the shared corridor and/or antechamber.

Since significant radiation in the form of higher-energy photon radiation, for example, can occur in an irradiation chamber because of the radiation treatment, the treatment chambers are constructed with radiation shielding such that other areas of the particle therapy installation (e.g., the corridor and/or antechamber) are not subjected to the radiation occurring in the irradiation chamber.

This is partly made possible by thick walls, which at least partly surround the irradiation chamber. Furthermore, solutions are known in which the access to the irradiation chamber is implemented by a serpentine or labyrinthine access path into which ceiling curtains can be drawn in some cases. This prevents the irradiation occurring in the irradiation chamber from penetrating to the outside through the serpentine or labyrinthine access path. Such access to an irradiation chamber is known, for example, from WO 2004/013865 A1.

SUMMARY AND DESCRIPTION

The present embodiments may obviate one or more of the drawbacks or limitations in the related art. For example, in one embodiment, a particle therapy system in which a shielding of treatment chambers is implemented in a simple, safe and low-cost way, which allows a space-saving arrangement of the treatment chambers and makes for a simple access path to an irradiation chamber, is provided.

The particle therapy system includes: at least one irradiation chamber, in which an object is irradiated with a treatment beam; an antechamber, which is shielded from radiation occurring in a radiation chamber and from which there is access to the at least one irradiation chamber; and at least one access area to the at least one irradiation chamber, which connects the irradiation chamber to the antechamber, with a radiation-protection door being arranged in the access area The access area is the area that makes access to the irradiation chamber possible. In routine operation, patients are moved for irradiation via the access area into the irradiation chamber or moved out of the irradiation chamber again after irradiation. In one embodiment, the irradiation chamber includes one access area.

In one embodiment, the geometry of the access area is configured such that a patient bed is able to be moved from the antechamber to the irradiation chamber along a path of travel in the access area that is substantially rectilinear.

A serpentine or labyrinthine access path, as known from the prior art, allows an effective radiation shielding but also has disadvantages. The serpentine or labyrinthine access path occupies a comparatively large amount of space in a particle therapy system. Since an access path is also formed by comparatively thick radiation protection walls, the particle therapy system becomes larger, and higher costs arise when building the particle therapy system. A serpentine or labyrinthine access path, which is usually several meters in length, also causes difficulties in handling a patient bed with a patient when the patient is being moved from the antechamber into the irradiation chamber or vice versa.

In one embodiment, a radiation protection door is arranged in the access area. The radiation protection door consequently ensures that, even with a simple geometry of the access area, radiation cannot escape from the radiation chamber to other chambers of the particle therapy installation. The radiation protection door dispenses with serpentine winding paths, one of the purposes of which is to provide radiation shielding. The costs arising for the radiation protection door are saved by the space saved by the simpler construction of the particle therapy system. The radiation protection door shields against a radiation, which for access areas with simple geometry, would otherwise penetrate more and more into the antechamber.

In one embodiment, the radiation protection door is configured such that the radiation arising in the irradiation chamber, which penetrates through the radiation protection door, is attenuated at least by a factor of 50. In other embodiments, the radiation arising in the irradiation is attenuated by at least a factor of 75 or at least a factor of 100, respectively. In this way, the antechamber is sufficiently protected against radiation (e.g., against fast neutrons and thermal neutrons arising during irradiation) even if irradiation is being carried out with carbon ions in the irradiation chamber, and a high radiation load arises by comparison with protons.

In one embodiment, the radiation protection door is made from steel. In one embodiment, steel with a thickness of approximately 45 cm is used for shielding from the radiation arising during a particle therapy. However, other materials may also be used. In one embodiment, the radiation protection door may have a thickness of at least 50 cm. In other embodiments, the radiation protection door may have a thickness of at least 75 cm or at least 100 cm, respectively.

In one embodiment, the geometry of the access area is configured in such a way that the path of travel in the access area is substantially rectilinear. Substantially rectilinear may be defined as a path in the access area that is configured such that a patient bed, when being moved along the path in the access area, makes insignificant turns (e.g., less than 40°, 30°, or 20°) or does not make any turns at all. Further turns are made, if at all, during the transition from the antechamber to the access area or from the access area to the irradiation chamber.

In one embodiment, the access area is configured such that after the radiation protection door, the patient bed is turned when moved from the access area into the irradiation chamber (e.g., after a patient bed has been moved through the radiation protection door, the patient bed is turned again, if at all, if the patient bed is moved from the access area into the irradiation chamber in which the actual irradiation takes place. A serpentine or zigzag movement is avoided by the more compact construction described above.

In one embodiment, the access area opens out at a sharp angle into the irradiation chamber, by which a part radiation shielding of the access area from the irradiation chamber is produced. This allows a space-saving construction and also simple handling of a patient bed during transport through the access area.

In one embodiment, the path in the access area may have a length of less than 10 m or, in another embodiment, less than 8 m.

A particle therapy system may include further treatment rooms, each of which is accessible via a corresponding further access area from the antechamber. Each of the access areas may be configured in accordance with the designs described above, with a radiation protection door and a rectilinear access path. Both radiation protection and low production costs as a result of a space-saving construction and simple handling of a patient bed to access each of the treatment rooms and access areas configured as described above may be provided.

In one embodiment, the access area to the irradiation chamber is arranged spatially so that a patient bed has to make a turn when being transferred from the access area to the irradiation chamber. Less radiation reaches the access area from the irradiation area in the irradiation chamber, allowing the radiation protection door arranged in the access area to be configured in a simpler and lower-cost manner.

In one embodiment, a radiation-protection wall is arranged between the irradiation chamber and the access area, by which the radiation protection door is protected against direct radiation, which goes out from an irradiation center in the irradiation chamber. The radiation-protection wall also enables the dimensions of the radiation protection door to be narrower, since a part of the radiation is shielded off by the radiation-protection wall.

In one embodiment, the irradiation chamber includes a wall projection such that a niche is formed in which neutrons generated and emitted by the irradiation are captured.

In one embodiment, the radiation protection door may be embodied as a sliding door, which allows simple handling and rapid opening or closing of the radiation protection door.

In one embodiment, the antechamber is a corridor configured such that direct access from the antechamber to further rooms and/or corridors of the particle therapy system is possible. For example, further treatment rooms may each be accessible from the antechamber via an access area. Other rooms of the particle therapy system, such as therapy planning rooms, lounges for patients for doctors, preparation rooms and/or examination rooms for patients or further passageways of the particle therapy system, may also be accessible from the antechamber in a direct manner.

In one embodiment, the antechamber is not a single room enclosed by walls. The antechamber may, for example, be connected to other passageways/rooms of a particle therapy system without a dividing door. In one embodiment of the particle therapy system, the antechamber may be divided up into a number of smaller rooms or corridors.

For additional radiation protection, the access area may be divided from the antechamber by an additional door, which is thinner than the radiation protection door. The additional door may, for example, be a polyethylene door (a PE door), which may include boron. The PE door provides effective shielding from thermal neutrons, which might still be present. Effective shielding from the fast neutrons may be provided by the radiation protection door.

DETAILED DESCRIPTION

Figure 1:
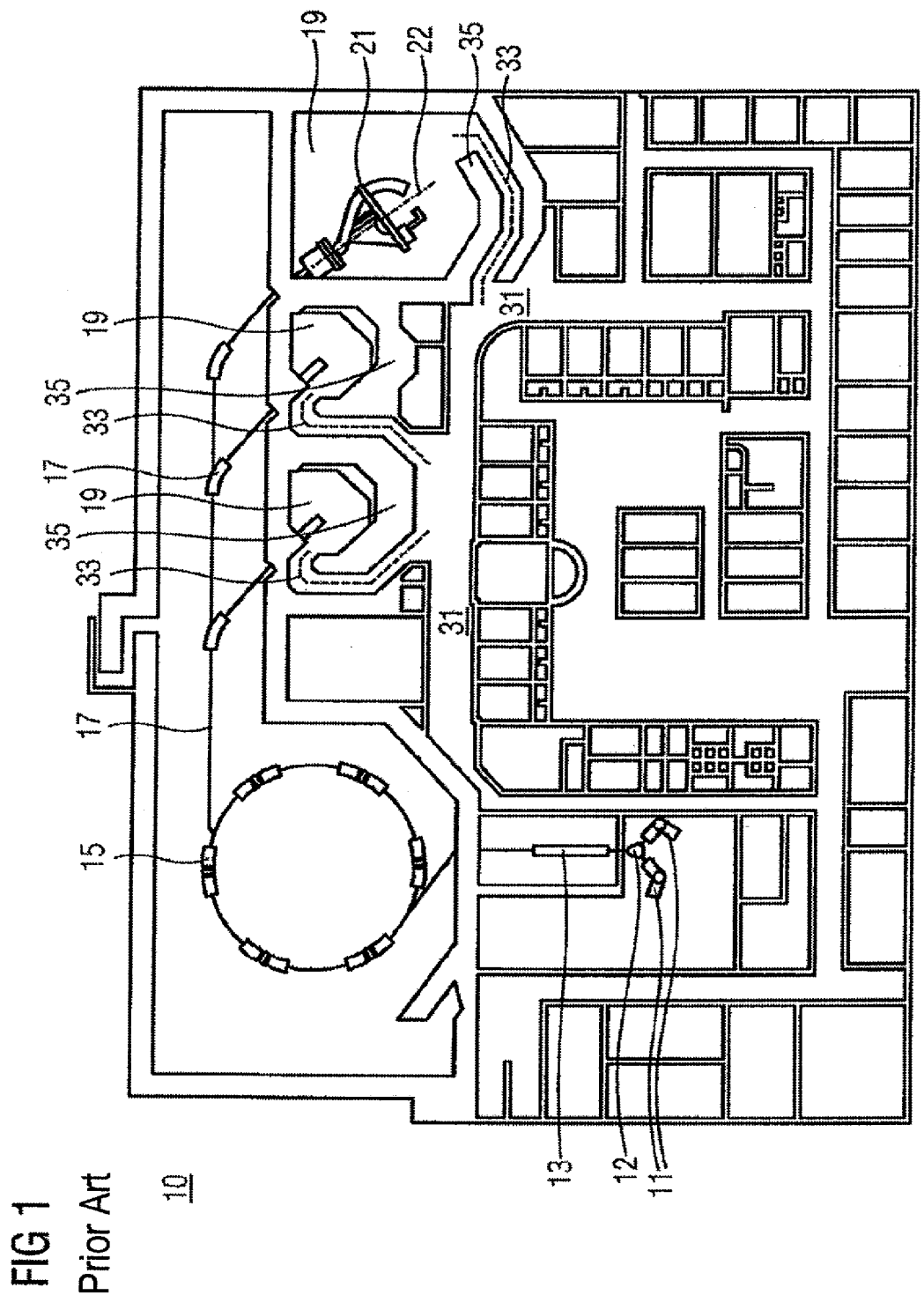
FIG. 1 shows a schematic view of a particle therapy system known from the prior art.

FIG. 1 shows a schematic view of the structure of a particle therapy system 10, as is known from the prior art. In the particle therapy system 10, a body (e.g., tumorous tissue in the body) is irradiated with a particle beam.

Ions such as, for example, protons, pions, helium ions, carbon ions or other sorts of ions, are used as particles. The particles are created in a particle source 11. If, as shown in FIG. 1, two particle sources 11, which generate two different types of ions, are provided, a switchover may be made within a very short time between the two different types of ions. A switching magnet 12, which is arranged between the ion source 11 and a pre-accelerator 13, may be used for the switchover. This allows the particle therapy system 10 to be operated with protons and with carbon ions at the same time, for example.

The particles generated by the particle source 11, or by one of the particle sources 11 and selected by the switching magnet 12 are accelerated in a pre-accelerator 13 up to a first energy level. The pre-accelerator 13 is a linear accelerator, for example. Subsequently, the particles are fed into an accelerator 15, for example, a synchrotron or cyclotron. In the accelerator 15, the particles are accelerated to high energies for irradiation. After the particles have left the accelerator 15, a high-energy beam transport system 17 conducts the particles to one or more irradiation chambers 19. In an irradiation chamber 19, the accelerated particles are directed onto a body to be irradiated. The accelerated particles are directed onto a body to be irradiated from a fixed direction (e.g., in fixed beam chambers) or from different directions via a gantry 21, which permits rotational movement around an axis 22.

A total of three treatment rooms 19 are shown in FIG. 1. The treatment rooms 19 are reached from a shared antechamber 31 (e.g., a corridor). The treatment chambers 19 are each accessed via an access area 33. A patient bed, which is moved from the shared antechamber 31 to one of the treatment chambers 19, is moved along a winding or serpentine path (e.g., shown in FIG. 1 as a dashed line) in the access area 33. After the patient bed has been moved along the serpentine path, the patient bed reaches the irradiation chamber 19. The treatment chambers 19 are surrounded by radiation protection walls, sometimes meters thick, so that no or little radiation penetrates from the treatment chambers 19 into the shared antechamber 31. As a result of the serpentine path in the access areas 33, no radiation escapes to the outside via the access areas 33. The access areas 33, therefore, occupy a great deal of space, which is surrounded by radiation protection walls, giving rise to comparatively high costs.

Figure 2:
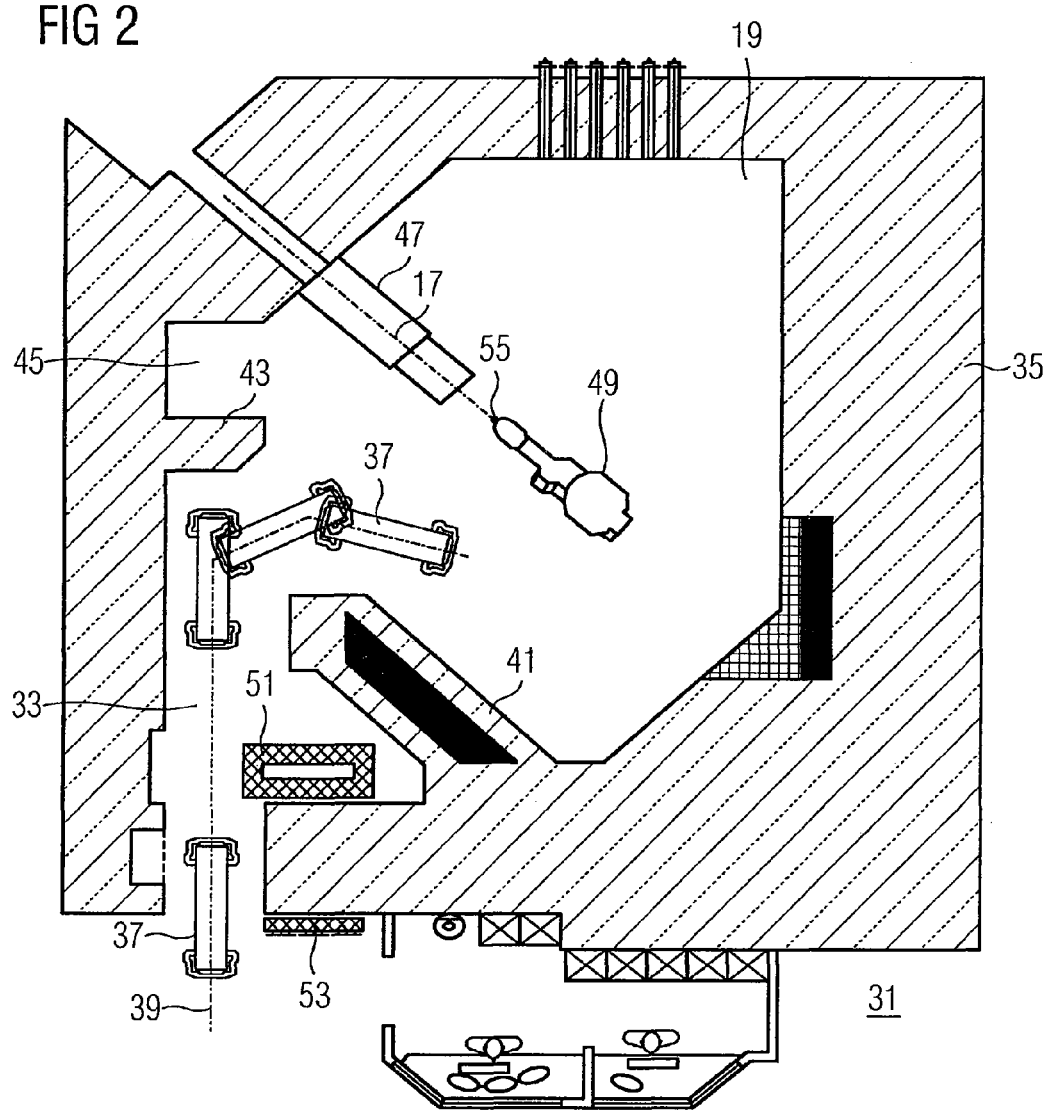
FIG. 2 shows a schematic view of one embodiment of an irradiation chamber with an access area that has a rectilinear access path.

FIG. 2 shows one embodiment of an irradiation chamber 19. One irradiation chamber 19 with surrounding structures is shown in greater detail in FIG. 2. A particle therapy system with such an irradiation chamber 19 may otherwise be constructed in a similar manner to the particle therapy system shown in FIG. 1.

The irradiation chamber 19, in which a patient is to be treated, is surrounded by radiation protection walls 35. Irradiation facilities are positioned within the irradiation chamber 19. In one embodiment, the irradiation facilities are positioned using a positioning apparatus (e.g., a robot arm 49). A patient lying on a patient bed 37 is positioned in a desired position by the robot arm 49 in accordance with a treatment plan in relation to a beam exit channel 47. A treatment beam (e.g., indicated as a dashed line in FIG. 1) is taken from the high-energy beam transport system 17 to the beam exit channel 47, exits from the beam exit channel 47 and hits an object to be irradiated.

With the irradiation chamber 19 shown in FIG. 2, entry from an antechamber 31 is also via an access area 33.

In one embodiment, a path 39, along which a patient bed is moved in the access area 33, is approximately configured as a rectilinear path. The path 39 is shown as a dashed line in FIG. 2. The patient bed is turned in the threshold area between the access area 33 and the irradiation chamber 19. So that no radiation gets out into the antechamber 31 from the irradiation chamber 19 via the access area 33 despite the simple geometry, a radiation protection door 51 is arranged in the access area 33. Movement in the access area 33 may be such that the irradiation chamber 19 and for the most part, also the access area 33, may be radiation-shielded from the other rooms of the particle therapy system (e.g., the antechamber 31). During the irradiation process, the antechamber 31 and other rooms of the particle therapy system 10 are protected from radiation arising in the radiation chamber 19. In one embodiment, the radiation protection door 51 has a thickness of 1 m, with a width of 2 m.

As a result of the radiation protection door 51, the access area 33 may be configured with a simple geometry so that a path running with an approximately rectilinear course is provided in the access area. The path may also be significantly shorter compared to serpentine or labyrinthine access areas.

In one embodiment, a further door 53 may be arranged between the antechamber 31 and the entry into the access area 33. Thus, the access area 33 may also be closed off without the comparatively large and heavy radiation protection door 51 having to be moved. In addition, the further door may shield against thermal neutrons as well.

A further radiation shielding wall 41 is arranged between the irradiation chamber 19 and the access area 33 so that radiation arising in an irradiation center 55 cannot strike the radiation protection door 51 directly. The radiation-protection wall 41 simultaneously forms a niche in which the radiation protection door 51 may be positioned if the access area 33 is to be opened. In one embodiment, the radiation protection door 51 is a sliding door. The radiation-protection wall 41 also forms a part of the boundary of the passageway of the access area 33.

The irradiation chamber 19 also includes a wall projection 43, through which a niche 45 is formed. The niche 45 is used to capture neutrons, which arise during the irradiation and are scattered at an angle (e.g., 60°) to the beam axis, and to prevent the neutrons from hitting other objects or reaching the outside.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A particle therapy system comprising:
an irradiation chamber, in which an object is irradiated with a treatment beam; an antechamber that is shielded from radiation occurring in the irradiation chamber; and an access area to the irradiation chamber, the access area connecting the irradiation chamber to the antechamber so that access from the antechamber to the irradiation chamber is via the access area, wherein a radiation protection door is arranged in the access area, wherein the access area is configured such that a path, along which a patient bed is moved from the antechamber to the irradiation chamber, is rectilinear, the path being configured such that the patient bed only makes turns of forty degrees or less along the path, and wherein the rectilinear path has a length of less than 10 meters.

2. The particle therapy system as claimed in claim 1, wherein the access area is arranged spatially in relation to the irradiation chamber such that the access area opens out at an acute angle into the irradiation chamber.

3. The particle therapy system as claimed in claim 1, further comprising a radiation-protection wall arranged between the irradiation chamber and the access area, the radiation-protection wall protecting the radiation protection door from direct radiation that goes out from an irradiation center in the irradiation chamber.

4. The particle therapy system as claimed in claim 1, wherein a wall projection is arranged in the irradiation chamber such that the wall projection forms a niche in which neutrons generated and emitted during irradiation are captured.

5. The particle therapy system as claimed in claim 1, wherein the radiation protection door attenuates the radiation occurring in the irradiation chamber and penetrating the radiation protection door by at least a factor of 50.

6. The particle therapy system as claimed in claim 1, wherein the radiation protection door has a thickness of at least 50 cm.

7. The particle therapy system as claimed in claim 1, wherein the radiation protection door is a sliding door.

8. The particle therapy system as claimed in claim 1, wherein the access area is separated from the antechamber by an additional door, the additional door being thinner than the radiation protection door.

9. The particle therapy system as claimed in claim 1, wherein the antechamber is configured such that further rooms, further corridors, or both further rooms and further corridors of the particle therapy system are directly accessible from the antechamber.

10. The particle therapy system as claimed in claim 2, further comprising a radiation-protection wall arranged between the irradiation chamber and the access area, the radiation-protection wall protecting the radiation protection door from direct radiation that goes out from an irradiation center in the irradiation chamber.

11. The particle therapy system as claimed in claim 4, further comprising a radiation-protection wall arranged between the irradiation chamber and the access area, the radiation-protection wall protecting the radiation protection door from direct radiation that goes out from an irradiation center in the irradiation chamber.

12. The particle therapy system as claimed in claim 2, further comprising a wall projection arranged in the irradiation chamber such that the wall projection forms a niche in which neutrons generated and emitted during irradiation are captured.

13. The particle therapy system as claimed in claim 3, further comprising a wall projection arranged in the irradiation chamber such that the wall projection forms a niche in which neutrons generated and emitted during irradiation are captured.

14. The particle therapy system as claimed in claim 3, wherein the radiation protection door attenuates the radiation occurring in the irradiation chamber and penetrating the radiation protection door by at least a factor of 50.

15. The particle therapy system as claimed in claim 3, wherein the radiation protection door is a sliding door.

16. The particle therapy system as claimed in claim 5, wherein the radiation protection door is a sliding door.

17. The particle therapy system as claimed in claim 6, wherein the access area is separated from the antechamber by an additional door, the additional door being thinner than the radiation protection door.

18. The particle therapy system as claimed in claim 4, wherein the antechamber is configured such that further rooms, further corridors, or both further rooms and further corridors of the particle therapy system are directly accessible from the antechamber.

* * * * *